United States Patent [19]

Florez et al.

[11] Patent Number: 4,655,222

[45] Date of Patent: Apr. 7, 1987

[54] COATED SURGICAL STAPLE

[75] Inventors: Hugo R. Florez, Somerset; Robert J. Tannhauser, Piscataway, both of N.J.

[73] Assignee: Ethicon, Inc., Somerville, N.J.

[21] Appl. No.: 635,763

[22] Filed: Jul. 30, 1984

[51] Int. Cl.$^4$ .............................................. A61B 17/04
[52] U.S. Cl. ............................. 128/334 R; 128/335.5; 227/DIG. 1; 411/920
[58] Field of Search ....................... 128/334 R, 335.5; 227/DIG. 1; 411/920

[56] References Cited

U.S. PATENT DOCUMENTS

| | | | |
|---|---|---|---|
| 3,080,564 | 3/1963 | Strekopitov et al. | 227/19 X |
| 3,589,589 | 6/1971 | Akopov | 227/19 X |
| 4,275,813 | 6/1981 | Noiles | 206/339 |
| 4,351,466 | 9/1982 | Noiles | 227/8 |
| 4,362,162 | 12/1982 | Nakajima et al. | 128/334 R |
| 4,467,805 | 8/1984 | Fukuda | 128/334 C |

Primary Examiner—Lucille M. Phynes
Attorney, Agent, or Firm—Charles J. Metz

[57] ABSTRACT

Sterile surgical staples for use with a stapling instrument with the surface of the staple coated with a low molecular weight fluorocarbon polymer.

5 Claims, 7 Drawing Figures

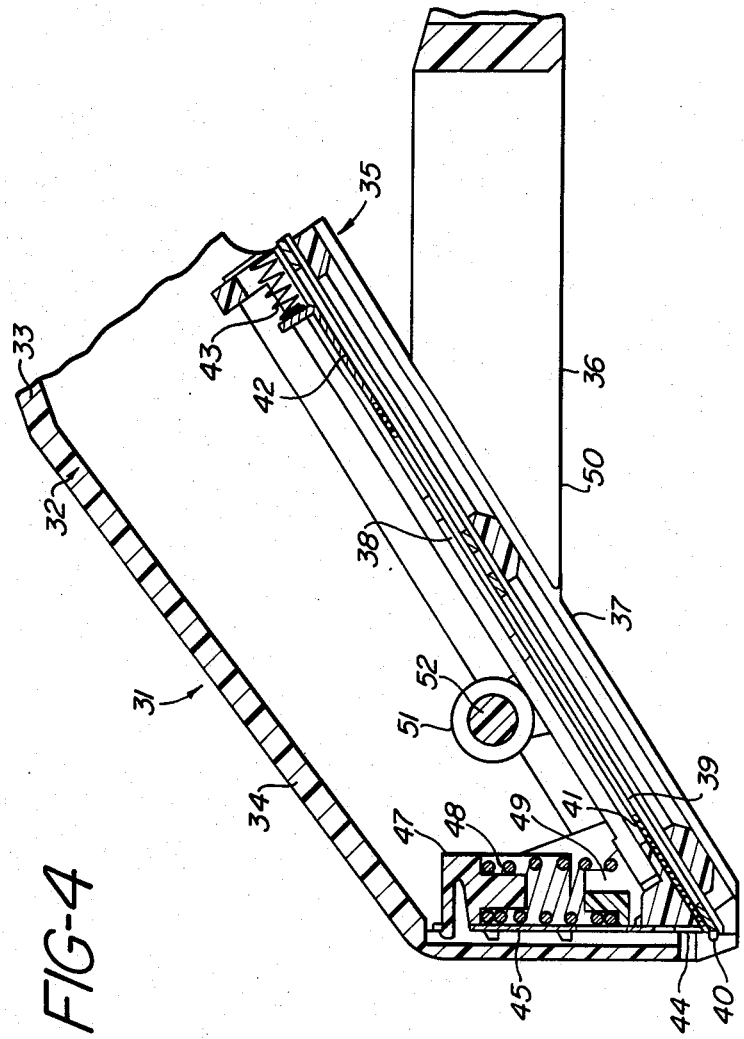

COATED SURGICAL STAPLE

The invention relates to the use of a low molecular weight fluorocarbon polymer as a coating for a metallic surgical staple, to the use of the coated staple in a stapler, and to the use of such coated staple in a procedure for closing wounds.

DESCRIPTION OF THE PRIOR ART

Surgical stapling instruments which are actuated in a repetitive manner to discharge and form a series of surgical staples are well known. Such stapling instruments have found considerable acceptance in the closing of wounds to the skins of humans and animals. The staples themselves are metal staples and are made from stainless steel, tantalum, or other biologically acceptable metal. In prior commercial practice, the staples have often been coated with a soap composition or with a high molecular weight polytetrafluoroethylene ("TEFLON") coating, to assist in both the placement of the staple and/or the function of the stapling instrument. There is, however, room for improvement in the performance of both materials. Soap, being bioabsorbable, tends to be absorbed from the implanted staple so that some tissue adhesion to the staple can begin to occur after wound healing begins; this tends to make staple removal more traumatic and painful. TEFLON tends to collect at the anvil, and in a multiple fire stapler, jamming can occur. In the commercialized version, the TEFLON coating is sprayed on the array of staples after the staples have been loaded into the stapler. The coating is present as discrete particles on only one side of the staple. It serves only as a mechanical lubricant and has little or no effect on the staple performance in the wound.

Noiles, in U.S. Pat. No. 4,275,813, discloses a coherent stack of surgical staples bonded together in parallel contiguous relationship by a plastic adhesive that can be, inter alia, "halogenated polyalkylenes such as polytetrafluoroethylene . . ."

Bogaty et at., in U.S. Pat. No. 4,012,551, discloses razor blades having the cutting edges thereof coated with a mixture of two fluorocarbon polymers, one of which can be a low molecular weight fluorinated hydrocarbon polymer (referred to in the patent as a "fluorocarbon telomer").

Homsy et al., in an article entitled "REDUCTION OF TISSUE AND BONE ADHESION TO COBALT ALLOY FIXATION APPLIANCES", J. Biomed. Mater. Res. 6, 451–464 (1972), disclose the use of high molecular weight polytetrafluoroethylene as a coating on internal fixation appliances to reduce tissue adhesion to such appliances.

Zambelli et al., in U.S. Pat. No. 3,977,081, disclose the use of a layer of polytetrafluoroethylene on a dental implant for the purpose of enabling an optimum epithelial adhesion to be generated between the implant and the surrounding mucosa and fibromucosa.

Everett, in U.S. Pat. No. 2,814,296, discloses polytetrafluoroethylene coated surgical needles.

The commercial manufacturer of low molecular weight polytetrafluoroethylene (referred to by the manufacturer as a "fluorotelomer") recommends that it be used in a number of industrial lubricating and release applications, including a heavy duty release agent for application to industrial equipment such as presses and rolls, especially in the manufacture and processing of hardboard, plywood, laminated wood products, and related materials. It is also recommended for use as a thickener for synthetic oils and other types of liquid lubricants to produce greases.

BRIEF SUMMARY OF THE INVENTION

The invention provides a surgical metallic staple coated with a thin layer of a low molecular weight fluorocarbon polymer, an array of such coated staples, a surgical stapler containing such coated staples, and a method of closing a wound utilizing such a coated staple, especially in those wound closure cases wherein the staple will be removed after a predetermined degree of healing has occurred.

Among the advantages that are obtained from using the invention are that the surgical stapler containing the subject coated staples is less apt to jam after extended operation than is the case with surgical staples coated with materials such as silicone and high molecular weight polytetrafluoroethylene, (even though the low molecular weight polytetrafluoroethylene may collect at the anvil, this does not interfere with the operation of the instrument) the staples of the invention penetrate tissue quite readily and therefore minimize trauma associated with their use, the staples of the invention have little or no tendency to adhere to tissue while implanted in the body, and they can be withdrawn with relatively little effort. Also, the low molecular weight polytetrafluoroethylene is much more readily coated on individual staples, forms a more adherent coating thereon, and can be used with less add-on, than TEFLON.

BRIEF DESCRIPTION OF THE DRAWINGS

FIG. 4 is a cross-sectional view of an automatic stapling instrument showing sterile surgical staples of the invention loaded in said instrument;

DETAILED DESCRIPTION OF THE INVENTION

Figure 1:
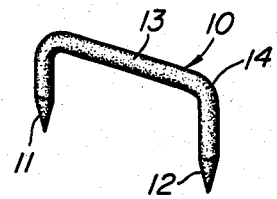
FIG. 1 is a perspective view of one form of sterile surgical staple in accordance with the invention.
Figure 2:
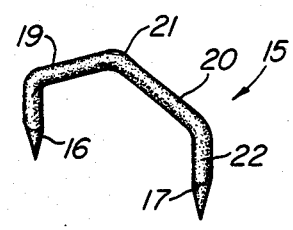
FIG. 2 is a perspective view of yet another form of a sterile surgical staple in accordance with the invention.

In FIG. 1 there is shown one configuration of a sterile surgical staple 10 of the invention. The staple comprises a pair of legs 11 and 12 connected at one end by a crown 13. In this embodiment, the crown is substantially perpendicular to the legs. Substantially all of the surface of the legs and crown is coated with a low molecular weight fluorocarbon polymer 14. In FIG. 2, the staple 15 comprises a pair of legs 16 and 17 joined at one end by a crown; however, in this configuration the crown comprises two sections 19 and 20 which extend angularly from the legs and are connected at the apex 21. Again, substantially the entire surface of the legs and crown is coated with a low molecular weight fluorocarbon polymer 22.

The low molecular weight fluorocarbon-coated staple is produced by initially forming the staple in its desired configuration by procedures known to the art. The staple is then cleaned, as by ultra-sonic cleaning, and is then coated with the fluorocarbon. The coating may be accomplished by coating the staple with a dispersion of the low molecular weight fluorocarbon polymer in a suitable liquid vehicle, such as trifluorotrichloroethane or similar halogenated liquid material, evaporating the liquid vehicle, and then, preferably, heating the coated staple to fuse the fluorocarbon polymer. The coating can be applied by immersing the staple in the dispersion, by spraying, or any other convenient method. After draining and air drying to remove most of the vehicle, the coated staple is then preferably heated to a temperature of from about 570° to 600° F. (299° to 316° C.) for 5 to 10 minutes to melt the polymer. This smooths out the coating, significantly improves the adhesion of the coating to the staple, and removes the remainder of the liquid vehicle for the polymer. Usually, the dispersion of polymer in the liquid vehicle will have a polymer solids content of from about 5 to 15 weight per cent (based on weight of the total disper although the exact proportion has not been found to be narrowly critical. An add-on of about 0.05 to about 0.2 weight per cent of the staple is usual. After coating, the staple may be sterilized by the usual procedures, such as ethylene oxide sterilization or exposure to gamma radiation from a radioactive source such as cobalt-60.

The low molecular weight fluorocarbon polymers are known in the art. They are sold commercially, usually in a dispersion of a halogenated liquid such as described above. They usually have molecular weights in the range of from about 2000 to about 50,000. The polymers contemplated are predominantly polymers of tetrafluoroethylene.

Figure 3:
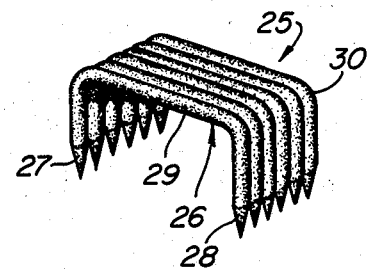
FIG. 3 is a perspective view of a stack of surgical staples of the invention.

In FIG. 3 there is shown a stack 25 of staples. Each staple 26 comprises a pair of legs 27 and 28 connected at one end by a suitable crown 29 with the surface of the legs and crown coated with a low molecular weight fluorocarbon polymer coating 30. The staples are stacked or butted side to side in a suitable array.

In FIG. 4 there is shown an automatic disposable skin stapling instrument. The instrument is loaded with low molecular weight fluorocarbon polymer coated sterile surgical staples of the invention. In FIG. 4 only the primary components of the surgical stapling instrument are shown. The stapling instrument 31 generally comprise a body 32 having a rear portion 33 which serves as the handle and a forward portion 34. The forward portion 34 of the instrument includes a surgical staple magazine indicated at 35. The instrument is actuated by the trigger mechanism 36. The magazine 35 is affixed to the lower edge of the forward portion of the body. The magazine comprises a lower member 37 and an upper member 38 with an anvil plate 39 located between these members. The anvil plate 39 terminates at its forward end in a coextensive anvil surface 40. Slidably mounted on the plate is a row of low molecular weight fluorocarbon polymer coated staples 41 of the invention. Also slidably mounted on the anvil plate 39 is a feeder shoe 42 which is constantly urged towards the anvil surface 40 by the double coil spring 43. The forward end of the magazine 35 provides a channel 44 for a staple driver 45 mounted within the forward portion of the instrument body. The staple driver 45 is affixed to a staple driver actuator 47. The trigger is operatively connected to the staple driver actuator to shift it and the staple driver 45.

A return spring 48 is located within the forward portion of the instrument body.

The upper end of the return spring is in contact with the staple driver actuator 47 and the lower end of the return spring is mounted on a return spring seat 49. The return spring is intended to bias the staple driver to its retracted position and at the same time to bias the trigger 36 to its normal position. The forward portion 50 of the trigger joins and is integral with a pivot pin 51. A portion of the pivot pin is adapted to be received in the side walls of the instrument body. The central portion of the pivot pin is of a reduced diameter as at 52. It provides clearance for the feeder shoe. Hence, the trigger 36 is pivotally fixed to the instrument body 32 and is operatively connected to the staple driver actuator 47 and the staple driver 45. Instruments of this type, are more fully described in U.S. Pat. Nos. 4,109,844 and 4,179,057 assigned to Senco Products Inc. and incorporated herein by reference. In operation of the stapling instrument, the trigger 36 is pressed and a staple 41 is formed about the anvil end 40 and inserted in the skin to close a wound. Once the staple is formed about the anvil 40 the trigger 36 is released and the instrument may be removed from the staple leaving the staple closing the wound.

Figure 5:
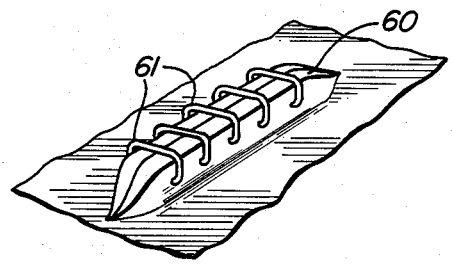
FIG. 5 is a perspective view of a wound closed using the sterile surgical staples of the invention.

In FIG. 5 there is a perspective view of a skin wound closure utilizing the staples of the invention. The incised section of the wound (60) is approximately in an everted orientation and the staples 61 formed along the length of the wound to close the wound.

Figure 6:
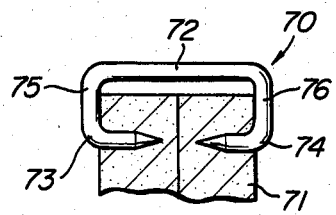
FIG. 6 is a cross-sectional view of a wound closed with a sterile surgical staple of the invention.
Figure 7:
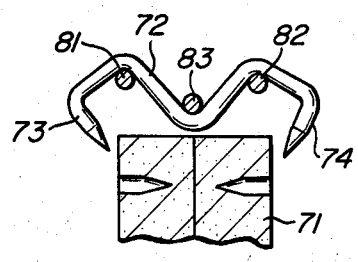
FIG. 7 is a cross-sectional view of a wound depicting the sterile surgical staple being removed from the healed wound.

FIG. 6 shows a staple 70 joining two sections of skin tissue 71 together. The staple is in its formed position. The staple has been bent at points along the crown 72 spaced from the legs 73 and 74 to form perpendicular areas 75 and 76 to allow the legs to be inserted into the skin. Once the wound is healed it is a relatively simple matter to remove the staple with an appropriate instrument. Such removal is schematically depicted in cross section FIG. 7. The extractor comprises a pair of parallel stationary prongs 81 and 82. These prongs are adapted so they will fit beneath the crown 72 of the staple at its bent points. The extractor also includes a movable central lever 83 which may be pushed between the stationary prongs. The prongs are placed beneath the crown and the central lever urged between the prongs or the prongs moved upwardly about the center lever. The staple shwon in FIG. 7 has been extracted from the wound.

In the example below, the low molecular weight fluorocarbon polymer employed was VYDAX Fluorotelomer 550, a 5 weight per cent dispersion in trichlorotrifluoroethane of a polytetrafluoroethylene having an average molecular weight of about 3700. The polymer per se has a density at 77° F. (25° C.) of 2.16 grams per cubic centimeter, a softening point (by ASTM E-28-58T) of 510° F. (265° C.), and a crystalline melting point of 572° F. (300° C.)

EXAMPLE 1 and CONTROL EXAMPLE 1

In this Example, steel surgical skin staples were compared with a commercial product, i.e., the same staples coated with soap. The staples of the invention were coated by dipping the staples, held on a strainer, into VYDAX 550 Fluorotelomer dispersion. The strainer holding the staples was removed from the VYDAX dispersion, drained, air dried for 16 hours, and then heated in an oven for 10 minutes at 305° C.

The staples were then loaded into a commercial surgical skin stapler, sterilized by exposure to gamma radiation, and then used in the following experiment:

Three healthy mature female Beagle dogs were anesthetized and prepared for aseptic surgery. Eight dorsal and five ventral midline full thickness skin incisions approximately 3.0cm in length were made in each dog. The cut edges of each incision were brought into apposition with subcuticular suture of 4-0 VICRYL. The dorsal skin incisions were closed with wide size soaped and Vydax coated staples and the ventral incisions were closed with regular size soaped and Vydax coated staples.

Four and seven days following surgery the dogs were anesthetized and the staples extracted. Photographs of the extractions were taken at the four day time period.

RESULTS

Visual and tactile differences in extraction characteristics between the soaped and Vydax coated skin staples were more pronounced at seven than four days postoperatively. The wide staples in the thicker dorsal skin provided extractions that were more demonstrably different than did the regular staples in the thinner ventral skin. Variances in wound healing also affected extraction differences. Wounds with greater amounts of escar formation masked differences in the staple extractions.

It was concluded that at seven days postoperatively Vydax coated (wide size) skin staples appeared to require less force for extraction than did soaped (wide size) skin staples, based in differences in visual and tactile observations. This distinction could not be made at four days.

After healing and scar tissue formation, the low molecular weight fluorocarbon polymer coated staples of the invention had apparently developed less adhesion to the healing tissue than the commercial soap-coated staples.

It has been noted in other experiments that the coated staples of this invention have little or no tendency to jam the stapler after repeated use. This is an improvement over high molecular weight silicone-coated surgical staples, which have not been commercialized for this reason.

EXAMPLE 2 and CONTROLS 2 and 3

Straight, pointed surgical staple wire blanks coated with VYDAX Fluorotelomer 550 by the procedure described above in Example 1, were compared to uncoated controls and TEFLON-coated controls (the TEFLON was sprayed on, to duplicate as closely as possible the commerical product), in the following experimert:

The force to insert and extract the staples in dog skin and in moleskin (adhesive-backed cotton flannel) was measured. The results are shown below in the table

TABLE I

|  | Dog Skin | | Moleskin |
| --- | --- | --- | --- |
|  | Insertion | Extraction | Extraction |
| Uncoated, Control 2 | | | |
| Average | 236 gms. | 7.9 gms | 83 gms |
| Range | 190–350 | 2–24 | 36–43 |
| Number Tested | 12 | 92 | 15 |
| TEFLON Coated, Control 3 | | | |
| Average | — | — | 41 gms. |
| Range | — | — | 18–64 |
| Number Tested | — | — | 12 |
| VYDAX Coated, Example 2 | | | |
| Average | 167 | 3.3 | 12 |
| Range | 100–205 | 0.1–10 | 1–38 |
| Number Tested | 12 | 112 | 15 |

We claim:

1. A sterile surgical staple for use with a stapling instrument in closing a wound of human or animal tissue comprising a pair of legs joined at one end by a crown with substantially the entire surface of said staple coated with a low molecular weight fluorocarbon polymer whereby it is easier to place said staple in said skin to close a wound and it is easier to remove said staple from said skin when the wound has healed.

2. The staple of claim 1 wherein the polymer is polytetrafluoroethylene.

3. In a surgical stapling instrument for implanting and forming surgical staples in the tissue of a patient, said instrument comprising a body, means for closing staples as they are driven into said tissue, a magazine for carrying a plurality of staples mounted on said body, and means for sequentially feeding staples from said magazine to said means for driving and closing the staples, the improvement which comprises the surface of said staples being coated with a low molecular weight fluorocarbon polymer.

4. The improvement according to claim 3 wherein the polymer is polytetrafluoroethylene.

5. A method of closing a wound in an animal which comprises using the staple of claim 1 to hold an approximated wound in position.

* * * * *